United States Patent [19]
Karimian et al.

[11] Patent Number: 5,847,118
[45] Date of Patent: Dec. 8, 1998

[54] METHODS FOR THE MANUFACTURE OF AMORPHOUS CEFUROXIME AXETIL

[75] Inventors: Khashayar Karimian, Mississauga, Canada; Mehrnoush Motamedi, San Diego, Calif.; Salvatore Zinghini, Downsview, Canada

[73] Assignee: Apotex, Inc., Weston, Canada

[21] Appl. No.: 900,669

[22] Filed: Jul. 25, 1997

[30] Foreign Application Priority Data

Jul. 26, 1996 [NZ] New Zealand ............................ 299077

[51] Int. Cl.⁶ .......................... C07B 63/00; C07D 501/34
[52] U.S. Cl. ............................................................. 540/222
[58] Field of Search ............................................... 540/222

[56] References Cited

U.S. PATENT DOCUMENTS

| | | | |
|---|---|---|---|
| 4,820,833 | 4/1989 | Crisp et al. | 540/222 |
| 5,013,833 | 5/1991 | Crisp et al. | 540/222 |
| 5,677,443 | 10/1997 | Zenoni | 540/215 |

FOREIGN PATENT DOCUMENTS 1571683  2/1976  United Kingdom .

*Primary Examiner*—Mark L. Berch
*Attorney, Agent, or Firm*—Nixon & Vanderhye PC

[57] ABSTRACT

A process for preparing pure amorphous cefuroxime axetil comprising the steps of dissolving crystalline cefuroxime axetil in a highly polar organic solvent and adding the resulting solution to water, or alternatively, dissolving crystalline cefuroxime axetil in a highly polar solvent and adding small quantities of water to the organic solution and adding the resulting organic-aqueous solution to water.

6 Claims, 2 Drawing Sheets

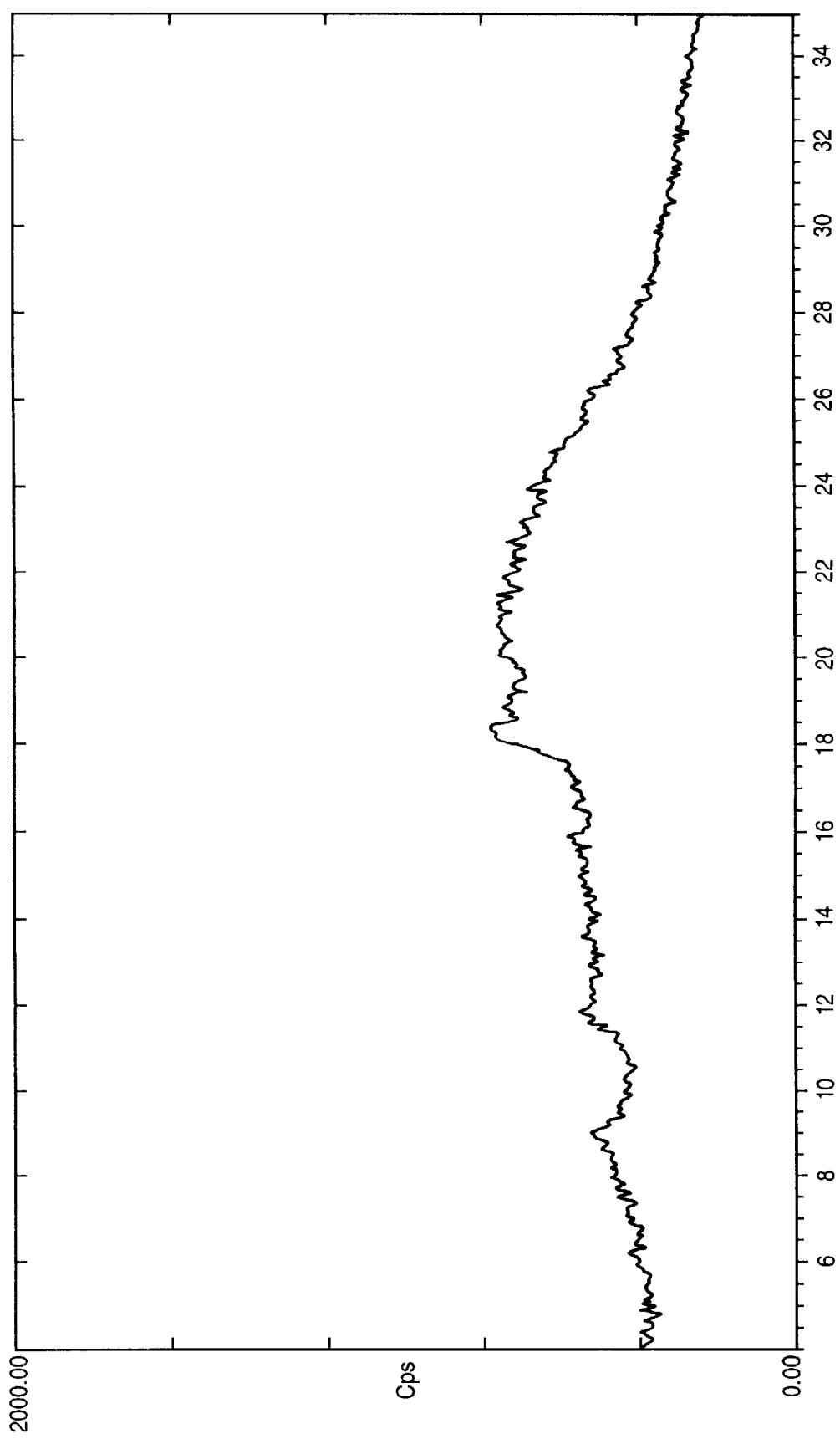
Fig. 1 Powder X-ray diffraction spectrum of amorphous cefuroxime axetil.

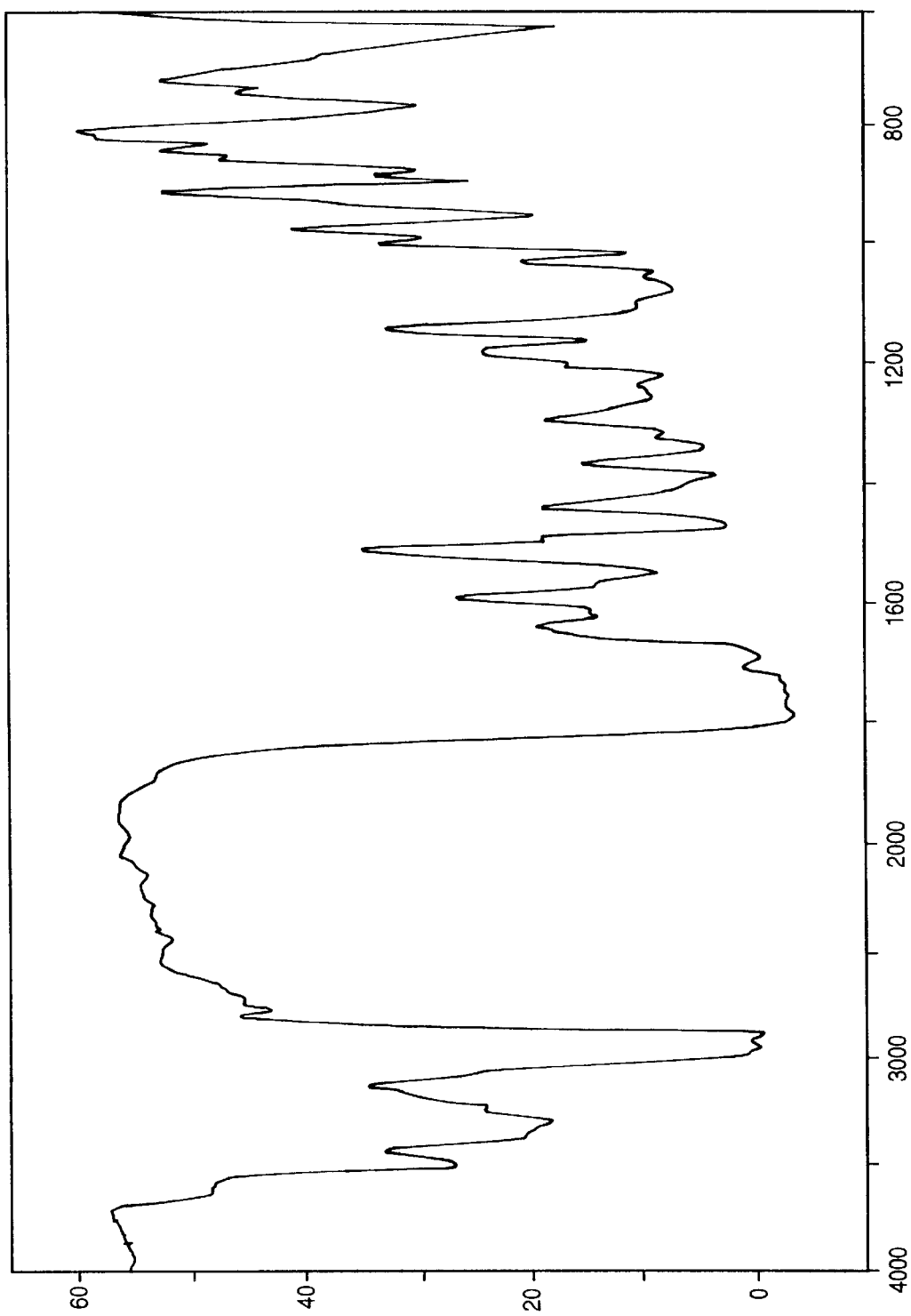

METHODS FOR THE MANUFACTURE OF AMORPHOUS CEFUROXIME AXETIL

FIELD OF THE INVENTION

This invention relates to novel processes for the manufacture of amorphous cefuroxime axetil.

BACKGROUND OF THE INVENTION

Cefuroxime axetil, [R-6α,7β(Z)]]-3-[[(aminocarbonyl)oxy]methyl]-7-[[2-furanyl-(methoxyimino)acetyl]amino]-8-oxo-5-thia-1-azabicyclo[4.2.0]oct-2-ene-2-carboxylic acid 1-acetoxyethyl ester is the 1-acethyloxyethyl ester of cefuroxime. Cefuroxime axetil can be classified as a member of the second generation cephalosporins and is β-lactam antibacterial agent. Cefuroxime axetil has the following structure (I)

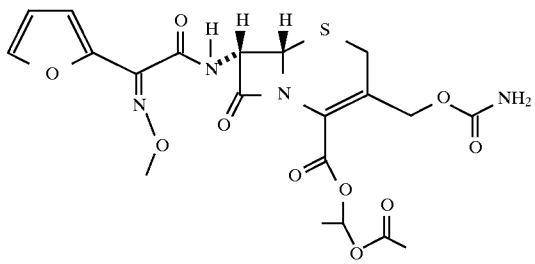

British Patent 1,571,683 discloses the preparation of cefuroxime axetil in crystalline form by precipitation from a solution of ethyl acetate with diethyl ether or diisopropyl ether. U.S. Pat. No. 4,820,833 also describes the preparation of cefuroxime axetil in crystalline form by crystallization from ethyl acetate with subsequent addition of dissopropyl ether to obtain more crystalline material.

U.S. Pat. No. 4,820,833 also discloses that the amorphous form of cefuroxime axetil has higher bioavailability than crystalline cefuroxime axetil while maintaining adequate chemical stability upon storage. Accordingly, for commercial purpose the amorphous form is used rather than the crystalline form.

In U.S. Pat. No. 4,820,833 (Ser. No. 938,140), the crystalline product is dissolved in an organic solvent and subsequently obtained in amorphous form by spray drying. Various examples of precipitation of amorphous cefuroxime axetil have also been provided.

U.S. Pat. No. 5,013,833 which issued out of a divisional application of Ser. No. 938,140 describes the preparation of amorphous cefuroxime axetil by solvent precipitation of the product dissolved in an organic solvent (or a mixture thereof in water).

In U.S. Pat. No. 4,820,833 and U.S. Pat. No. 5,013,833 the organic solvents include ketones, alcohols, acetonitrile, tetrahydrofuran, dioxane, esters, chlorinated solvents, or a homogeneous mixture of at least two such solvents.

The precipitation processes referred to in U.S. Pat. No. 5,013,833 while producing cefuroxime axetil substantially in amorphous form have a number of disadvantages:

1. The use of very large volumes of a solvent such as dichloromethane (40 ml/g) and diisopropyl ether (32.5 ml/g) that by their toxicity and possibility of explosive peroxide formation may render the process not commercially feasible.

2. Precipitation of the product dissolved in acetone from water requires very elaborate experimental set up in the laboratory (filtration of the solution of the product prior to its addition to water or spray drying, high rate of stirring, exact rate of addition, continuous froth collection, the necessity to harvest the product immediately) which renders the reaction arduous and difficult to manage in a large scale manufacturing environment. In fact, even under a manageable laboratory environment, only a substantially amorphous product could be obtained. Further, the amount of the crystalline form varies substantially with slight changes in the above-mentioned parameters.

It has now been surprisingly found that by dissolving crystalline cefuroxime axetil in a minimum volume of a highly polar organic solvent and adding the resulting solution to water or by dissolving crystalline cefuroxime axetil in a minimum volume of a highly polar organic solvent, adding water to the resulting solution and subsequently adding the resulting aqueous-organic solution to water, amorphous cefuroxime axetil could be obtained.

The present processes have a number of major advantages over the existing procedures.

First, because of excellent solubilizing properties of the highly polar solvents used in this invention, there is no need for filtration of the solution containing the product prior to its precipitation in amorphous form. Filtration is crucial in the precipitation processes disclosed in U.S. Pat. No. 5,013,833 because minute quantity of undissolved crystalline material could act as seeds and cause the precipitation of at least some of the material in its thermodynamically more stable crystalline form rather than the high energy amorphous form which may explain why only "substantially amorphous" material could be obtained by the previously disclosed precipitation processes.

Second, very small volume of a highly polar solvent is required to achieve total dissolution, thus rendering the present processes more economical and environmentally safe.

Third, the experimental conditions are simple and applicable to large scale production.

Fourth, the present processes are reproducible and consistently afford amorphous [as examined by powder x-ray diffraction and IR spectrum (FIGS. 1 and 2)].

Fifth, the amorphous product generated by the processes of the present invention is highly pure and shows an acceptable ratio of the R and S diasteroisomers as defined by U.S. Pharmacopoeia 23 (page 315). The mixture has improved solubility as compared with amorphous R isomer or amorphous S isomer alone.

Sixth, the yields of the amorphous product obtained when practising the invention are very high and within the range of 84 to 96%.

BRIEF DESCRIPTION OF THE INVENTION

Amorphous cefuroxime axetil is conveniently obtained by dissolving the crystalline form in a highly polar solvent such as DMSO, DMF, or preferably formic acid and adding the resulting solution at 0°–20° C. to water with stirring. The precipitated amorphous material is filtered, pulped in small quantities of water and filtered (twice) to remove residual polar solvent. The damp cake is then dried with forced nitrogen at 3°–35° C. and then under vacuum at 35° C. to obtain amorphous cefuroxime axetil in high yields. FIG. 1 is a X-ray powder diffraction of amorphous cefuroxime as produced by the invention. FIG. 2 is a IR spectrum of amorphous cefuroxime axetil.

DETAILED DESCRIPTION OF THE INVENTION

According to the present invention a process for the preparation of pure amorphous cefuroxime axetil is provided.

The starting material in the present invention is crystalline cefuroxime axetil and more particularly a 50:50 mixture of R and S isomers of the carbon forming the ester function with the 2-carboxyl group of cefuroxime, which is commercially available.

The amorphous cefuroxime axetil in accordance with the invention contains less than 0.6% of impurities. The major impurity associated with the process is usually in the range of 0.3–0.5% and is the anti form cefuroxime axetil in which the $CH_3$—O— group of the oxime is cis with the furil ring:

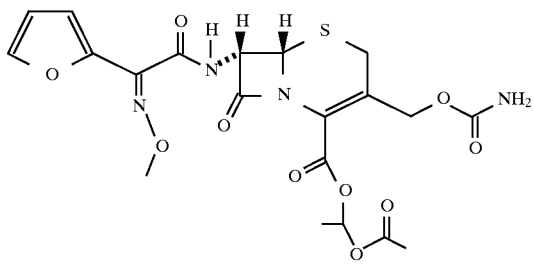

(I)

The amorphous form of cefuroxime axetil is a mixture of its R and S isomers in which the ratio of peak responses R should be between 0.48 and 0.55, as determined by the following equation.

$$R = r_A/(r_A + r_B)$$

The solvent or mixture of solvents employed to dissolve the crystalline form of cefuroxime axetil will be chosen among organic solvent of high polarity. Suitable solvents include dimethyl sulfoxide, dimethyl formamide, and preferably formic acid. The solvent if desired may be heated. The concentration of cefuroxime axetil in the solvent is as high as possible and preferably no less than 0.3 g/ml of the solvent.

The process comprises the dissolution of crystalline cefuroxime axetil in a highly polar organic solvent. The resulting solution is then added to water while stirring. Alternatively after dissolution of crystalline cefuroxime axetil, water may be added to the polar organic solution which is then added to water. The addition of the resulting solution to water is carried out between 0° and 40° C. and preferably between 0° and 4° C.

The amorphous cefuroxime axetil produced according to the invention has been identified by powder x-ray diffraction and IR spectroscopy (FIGS. 1 and 2).

The transition temperature for the conversion of the amorphous form of cefuroxime axetil to its crystalline form appears to be low. Accordingly, due caution must be exercised to maintain the vacuum oven temperatures of below 45° C. during the final drying stage.

The invention will be more fully understood by the following examples which illustrate the present invention, but are not to be considered limiting to the scope of the invention.

EXAMPLE 1

Cefuroxime axetil (5 g) was dissolved in 12 ml dimethyl sulfoxide by gentle heating. The resulting solution was added dropwise to deionized water (100 ml) cooled to 4° C. with good mechanical stirring. A thick slurry formed which was filtered and washed with a small quantity of ice cold deionized water. The damp cake was pulped in ice cold deionized water (30 ml) for 10 minutes, filtered and washed. Pulping was repeated once more. The cake was then dried under a stream of nitrogen for 42 hours and then dried under vacuum at 40°–45° C. for 48 hours. Yield 4.3 g (85%).

EXAMPLE 2

Cefuroxime axetil (5 g) was dissolved in 15 ml dimethyl sulfoxide by gentle heating. Deionized water (6 ml) was added with good stirring. The resulting solution was added dropwise to deionized water (90 ml) cooled to 4° C. with good mechanical stirring. A thick slurry formed which was filtered and washed with a small quantity of ice cold deionized water. The damp cake was pulped in ice cold deionized water (30 ml) for 10 minutes, filtered and washed. Pulping was repeated once more. The cake was then dried under a stream of nitrogen for 42 hours and then dried under vacuum at 40°–45° C. for 48 hours. Yield 4.7 g (95%).

EXAMPLE 3

Cefuroxime axetil (5 g) was dissolved in 20 ml dimethyl formamide by gentle heating. The resulting solution was added dropwise to deionized water (150 ml) cooled to 4° C. with good mechanical stirring. A thick slurry formed which was filtered and washed with deionized water. The damp cake was pulped in deionized water (100 ml) for 30 minutes, filtered and washed. Pulping was repeated once more. The cake was then dried under vacuum at 40°–45° C. for 48 hours. Yield 4.15 g (83%).

EXAMPLE 4

Cefuroxime axetil (5 g) was dissolved in 25 ml dimethyl formamide by gentle heating. Deionized water (9 ml) was added with good stirring. The resulting solution was added dropwise to deionized water (110 ml) cooled to 4° C. with good mechanical stirring. A thick slurry formed which was filtered and washed with a small quantity of ice cold deionized water. The damp cake was pulped in ice cold deionized water (30 ml) for 10 minutes, filtered and washed. Pulping was repeated once more. The cake was then dried under a stream of nitrogen for 42 hours and then dried under vacuum at 40°–45° C. for 48 hours. Yield 4.4 g (89%).

EXAMPLE 5

Cefuroxime axetil (100 g) was dissolved in 152 ml 88% cold formic acid. The resulting solution was added dropwise to ice cold deionized water (2000 ml) with good mechanical stirring. A thick slurry formed which was filtered and washed with a small quantity of ice cold deionized water. The damp cake was pulped in ice cold deionized water (400 ml) for 10 minute, filtered and washed. Pulping was repeated once more. The cake was then dried under a stream of nitrogen for 72 hours and then dried under vacuum at 40°–45° C. for 48 hours. Yield 90 g (90%).

EXAMPLE 6

Cefuroxime axetil (100 g) was dissolved in 105 ml 96% cold formic acid. The resulting solution was added dropwise to ice cold deionized water (2000 ml) with good mechanical stirring. A thick slurry formed which was filtered and washed with a small quantity of ice cold deionized water. The damp cake was pulped in ice cold deionized water (400 ml) for 10 minute, filtered and washed. Pulping was repeated once more. The cake was then dried under a stream of nitrogen for 72 hours and then dried under vacuum at 40°–45° C. for 48 hours. Yield 90 g (90%).

What is claimed is:

1. A process of preparing an amorphous cefuroxime axetil which comprises the steps of:

(a) dissolving crystalline cefuroxime axetil in a volume of a highly polar organic solvent only sufficient to dissolve it, and adding the resulting solution to water; or (b) dissolving crystalline cefuroxime axetil in a volume of a highly polar organic solvent only sufficient to dissolve it, adding water to the resulting solution and subsequently adding the resulting aqueous-organic solution to water;

wherein the highly polar organic solvent is selected from the group consisting of a sulfoxide, an amide and formic acid.

2. The process of claim 1 wherein the sulfoxide is dimethylsulfoxide.

3. The process of claim 1 wherein the amide is selected from the group consisting of dimethyl formamide, dimethylacetamide and hexamethyl phosphoramide.

4. The process of claim 1 wherein the solvent is a homogeneous mixture of dimethylsulfoxide and the amide.

5. The process of claim 1 wherein the addition of the resulting solution to water is carried out between 0° C. to 40° C.

6. The process of claim 5 wherein the addition is carried out between 0° to 40° C.

* * * * *

UNITED STATES PATENT AND TRADEMARK OFFICE
CERTIFICATE OF CORRECTION

PATENT NO.    : 5,847,118
DATED         : December 8, 1998
INVENTOR(S)   : Karimian et al.

It is certified that error appears in the above-identified patent and that said Letters Patent is hereby corrected as shown below:

Column 6,
Line 11, change "40ºC" to -- 4ºC --.

Signed and Sealed this

Twenty-seventh Day of August, 2002

Attest:

JAMES E. ROGAN
Attesting Officer     Director of the United States Patent and Trademark Office